Figure 1:
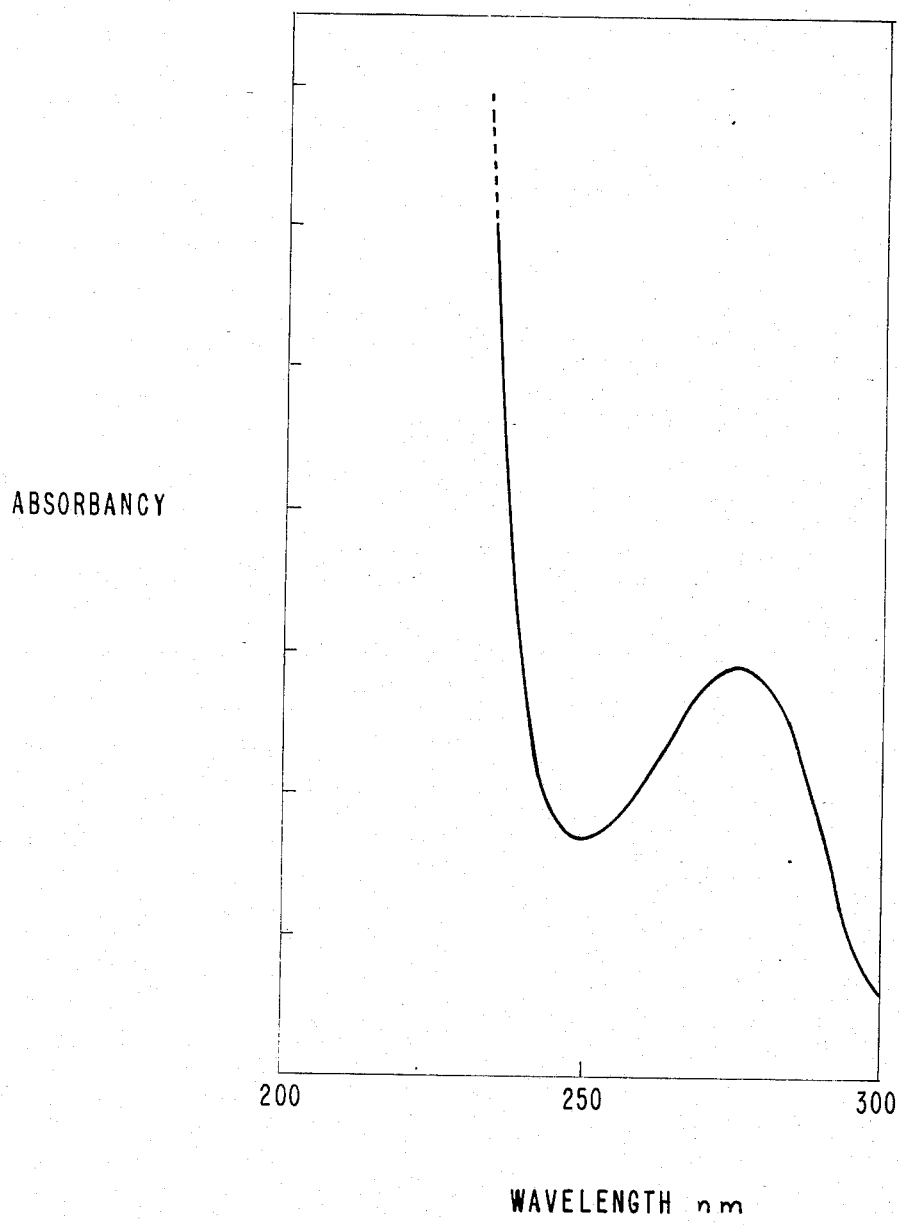

United States Patent [19]

Sugiyama et al.

[11] Patent Number: 4,634,763
[45] Date of Patent: Jan. 6, 1987

[54] AMYLASE INHIBITOR AND PREPARATION AND USE THEREOF

[75] Inventors: Masami Sugiyama; Yasushi Kasahara, both of Tokyo, Japan

[73] Assignee: Fujizoki Pharmaceutical Co., Ltd., Tokyo, Japan

[21] Appl. No.: 428,918

[22] Filed: Sep. 30, 1982

[30] Foreign Application Priority Data

Nov. 16, 1981 [JP] Japan ................................ 56-182316

[51] Int. Cl.$^4$ ........................ C07K 15/10; C07K 3/20
[52] U.S. Cl. .................................. 530/375; 530/372; 530/412; 530/413
[58] Field of Search ................ 260/112 R, 112 G, 121

[56] References Cited

U.S. PATENT DOCUMENTS

| | | | |
|---|---|---|---|
| 3,950,319 | 4/1976 | Schmidt et al. | 260/112 G |
| 4,282,318 | 8/1981 | Oedey et al. | 435/68 |
| 4,444,760 | 4/1984 | Thomas, Jr. | 424/177 |
| 4,451,455 | 5/1984 | Vertesy et al. | 435/68 |
| 4,463,091 | 7/1984 | Harada et al. | 435/68 |

OTHER PUBLICATIONS

Abstract, Oriental Yeast K.K., Niashin Flour Mill K.K., Alpha-amylase Inhibitor Derived from Wheat, 2-1-0-81.
C.A. #117184n, Niashin Flour Milling Co., Oriental Yeast Co. Ltd., α-Amylase Inhibitors, 4-8-82.
C.A. #30411a, Niashin Flour Milling Co., Isolation & Properties of an α-amylase Inhibitor from Wheat.
Biochim. Biophys. Acta., 391, 1975, Inhibition of Amylases . . . Kernal, pp. 170-178, Silame et al.
Biochim. Biophys. Acta, 658, 1981, Isolation and Characterization . . . α amylase, pp. 387-396, O'Connor et al.
Biochim. Biophys. Acta., 422, 1976, pp. 159-169, Purification of an α-amylase Inhibitor from Wheat, O'Donnell.
Gospodarowicz, D. et al., In Vitro, 14, 85-118 (1978).
"Purification of a Fibroblast Growth Factor from Bovine Pituitary", D. Gospodarowicz, vol. 250, No. 7, J. of Biological Chemistry, pp. 2515-2520 (1975).
"Purification and Partial Characterization of an Acidic Fibroblast Growth Factor from Bovine Pituitary", vol. 257, No. 16, J. of Biological Chemistry, Gambarini et al., pp. 9692-9697, (1981).
"Purification and Partial Characterization of Bovine Pituitary Fibroblast Growth Factor", Lemmon et al., J. of Cellular Biochemistry, vol. 21, pp. 195-208 (1983).
"Brain-derived Fibroblast Growth Factor: Identity with a Fragment of the Basic Protein of Myelin", Westall et al., Proc. Natl. Acad. Sci. USA, vol. 75, No. 10, pp. 4675-4678, Oct. 1978.
"Purification of the Fibroblast Growth Factor Activity from Bovine Brain", J. of Biochemistry, vol. 253, No. 10, pp. 3736-3743, 1978.
"Purification in High Yield of Brain Fibroblast Growth Factor by Preparative Isoelectric Focusing at pH 9.6*", Gospodarowicz et al., J. of Biological Chemistry, vol. 257, No. 20, pp. 12266-12276 (1982).
"Purification and Characterization of Acidic Fibroblast Growth Factor from Bovine Brain", Thomas et al., Proc. Natl. Acad. Sci. USA, vol. 81, pp. 357-361 (1984).

Primary Examiner—Morton Foelak
Assistant Examiner—Garnette D. Draper
Attorney, Agent, or Firm—Burgess, Ryan & Wayne

[57] ABSTRACT

A novel amylase inhibitor, obtained from hard wheat and durum wheat by using dye ligand affinity chromatography having an inhibitory activity on human salivary amylase of less than 0.1 of the inhibitory activity on human pancreatic amylase is disclosed which is useful for measuring isoenzymes of amylase in the field of clinical tests.

2 Claims, 10 Drawing Figures

FIG. I

AMYLASE INHIBITOR AND PREPARATION AND USE THEREOF

This invention relates to a novel amylase inhibitor and a process for producing the same.

Various amylase inhibitors are known but amylase inhibitors which specifically inhibit salivary amylase and also do not inhibit pancreatic amylase are not known. For instance, it is known that an amylase inhibitor is present in wheat (M. D. O'Donnel et al., Biochim. Biophys. Acta, Vol. 422, pp 159–169 (1976)). This amylase inhibitor inhibits not only salivary amylase, but also pancreatic amylase.

It has now been found that a novel amylase inhibitor, named Sain, which exhibits a ratio of the inhibition rate against pancreatic amylase to the inhibition rate against salivary amylase of less than 0.1, can be obtained from hard wheat and durum wheat using dye ligand affinity chromatography.

Since the amylase inhibitor Sain specifically inhibits salivary amylase, it is useful for measuring isoenzymes and can replace conventional electrophoresis procedures.

The grains of the above wheat are first milled and the wheat flour is mixed with water or an aqueous solution such as a buffer solution in an amount of 5 to 20 times the wheat flour by volume. The mixture is stirred for between 30 minutes and 2 hours, and then filtered or centrifuged to obtain the extract of tne amylase inhibitor. During extraction, the mixture may be heated to a temperature not exceeding the temperature at which the starch of the wheat becomes gelatinized.

The dye ligand affinity chromatography is carried out using the reation product of a reactive dye and a carrier having hydroxyl group or amino group as the packing. Such a carrier includes Sephalose 4B and Sephalose CL-6B (manufactured by Pharmacia AB), Sephadex G-200 (manufactured by Pharmacia AB), Bio-gel-P (manufactured by Bio Rad Co.), and cellulose.

The reactive dye is a derivative of cyanuric chloride, and includes reactive red and reactive blue.

The reaction of the reactive dye with the carrier may be carried out in the following manner. The carrier is suspended in water, and the suspension is made alkaline. Then, the reactive dye is added to the alkaline suspension, and the suspension is allowed to warm with gentle stirring. Thereupon, chloride of the cyanuric chloride moiety is reacted with the hydroxyl group or the amino group of the carrier, to thereby covalently bond the reactive dye to the carrier.

The amount of the reactive dye is usually about 0.1 to 1 gram per 100 ml of the carrier in a swelled form. The alkali added to the suspension may be sodium hydroxide, potassium hydroxide, sodium carbonate, etc., and the pH of the suspension is adjusted to between about 9 and 11. The reaction may be accelerated by heating. After the reaction, the carrier immobilized with the reactive dye is filtered off, and washed several times with a suitable solvent such as water or acetone.

The thus produced immobilized reactive dye is packed in a column, and a solution containing the amylase inhibitor Sain is passed through the column. Then, the adsorbates on the immobilized reactive dye are eluted by a developing agent. The amount of the amylase inhibitor fed to the column is preferably between 5 and 10 g per liter of the immobilized reactive dye. A phosphate buffer solution-acetone gradient and various gradients of a pyrophosphate buffer solution and a polar solvent such as ethanol, methanol and acetone may be employed as the developing agent. The effluent is fractionated by using an indicator such as ultraviolet absorption or the protein concentration determined by the Folin-Lowry method, and the fractions of the amylase inhibitor Sain are then collected. After the elution, the immobilized reactive dye may be regenerated according to known methods.

While it is known that an enzyme can be purified by dye ligand affinity chromatography, it has never been known that an enzyme inhibitor, such as the amylase inhibitor Sain, can be purified by using the dye ligand affinity chromatography. The inventors have found that the amylase inhibitor can be purified by this procedure, and other enzyme inhibitors may possibly be purified in this manner.

When the amylase inhibitor Sain is isolated from the extract of wheat flour, other purification methods may also be employed together with the dye ligand affinity chromatography. Such purification methods include ion-exchange chromatography, gel filtration, fractional precipitation using alcohol, fractional precipitation using ammonium sulfate, and dialysis which are general purification methods for proteins.

The amylase inhibitor Sain may be separated from other amylase inhibitors by using dye ligand affinity chromatography. At that time, most impurities are also removed from the amylase inhibitor Sain. The amylase inhibitor Sain in pure form is produced from the aqueous extract of the wheat by treating twice with the dye ligand affinity chromatography or by treating once with the affinity chromatography and then treating with ion-exchange chromatography.

The amylase inhibitor Sain obtained according to the manner described in Example 1 has the following properties.

1. Molecular weight

The molecular weight of the amylase inhibitor determined by means of gel filtration using Sephadex G-100 is between about 23,000 and 24,000. Since the molecular weight determined by means of electrophoresis using sodium dodecyl sulfate and polyacrylamide gel is between about 11,000 and 13,000, the amylase inhibitor Sain is believed to be a dimer.

2. Ultraviolet absorption spectrum

The ultraviolet absorption spectrum of a 0.22% aqueous solution of the amylase inhibitor was measured, and is shown in FIG. 1.

3. Infrared absorption spectrum

Figure 2:
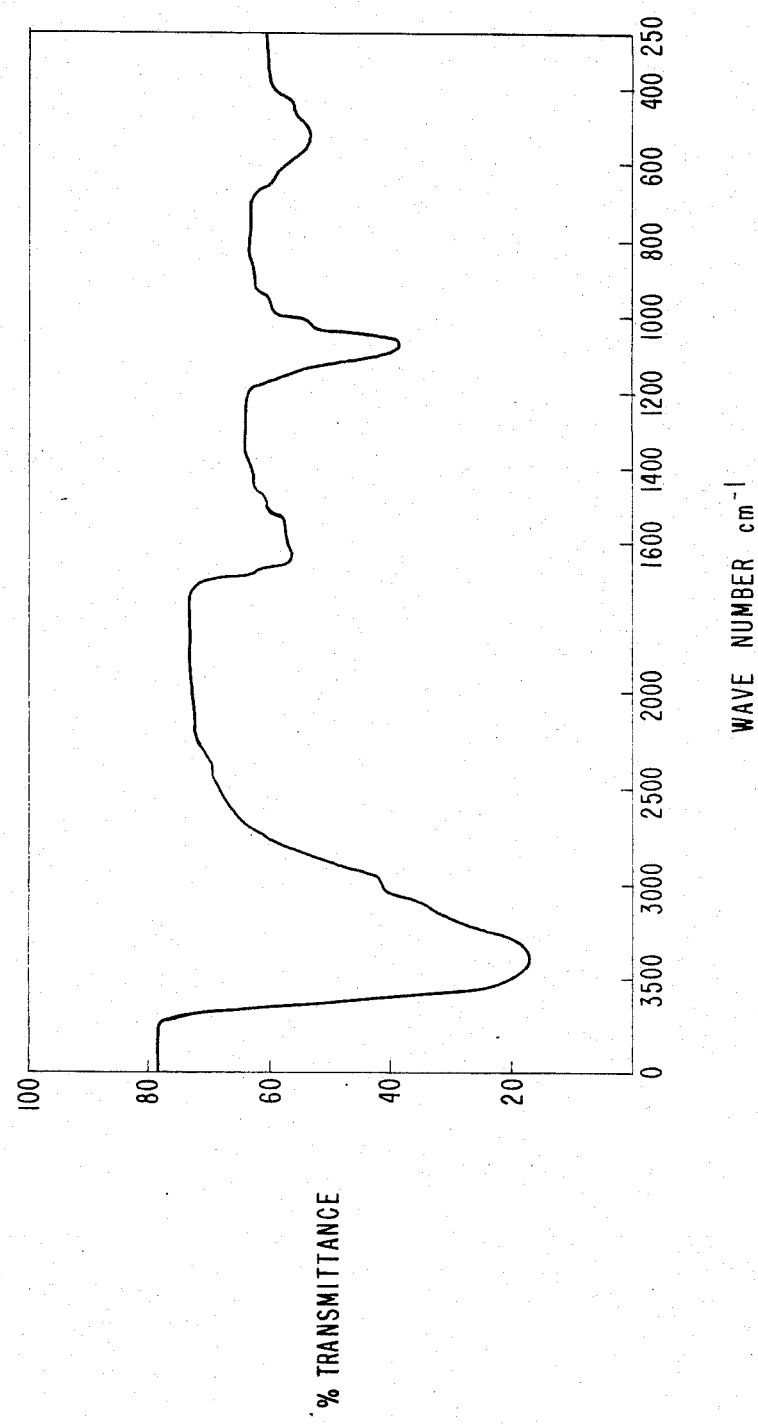

The infrared absorption spectrum of the amylase inhibitor when pelleted with potassium bromide was meaured, and is shown in FIG. 2.

4. Isoelectric point

The isoelectric point of the amylase inhibitor measured by using Bio Lyte (manufactured by Bio Rad Co.) is 5.0.

5. Content of carbohydrate

The carbohydrate content of the amylase inhibitor measured by means of the phenolsulfuric acid method is zero.

6. Amino acid composition

The amylase inhibitor was hydrolyzed with 6N hydrochloric acid at 110° C. for 22 hours, and the number of each amino acid of the hydrolyzate was determined. The amino acid composition estimated from the amino acid content and the molecular weight is as follows:

| Tyr | 17 | Ser   | 12 |
|-----|----|-------|----|
| Leu | 6  | Thr   | 6  |
| Ile | 4  | Asp   | 17 |
| Met | 10 | Arg   | 9  |
| Val | 24 | His   | 2  |
| Ala | 24 | Lys   | 9  |
| Gly | 22 | Phe   | 5  |
| Pro | 11 | ½ Cys | 14 |
| Glu | 22 |       |    |

7. Inhibition on amylase

Figure 3:
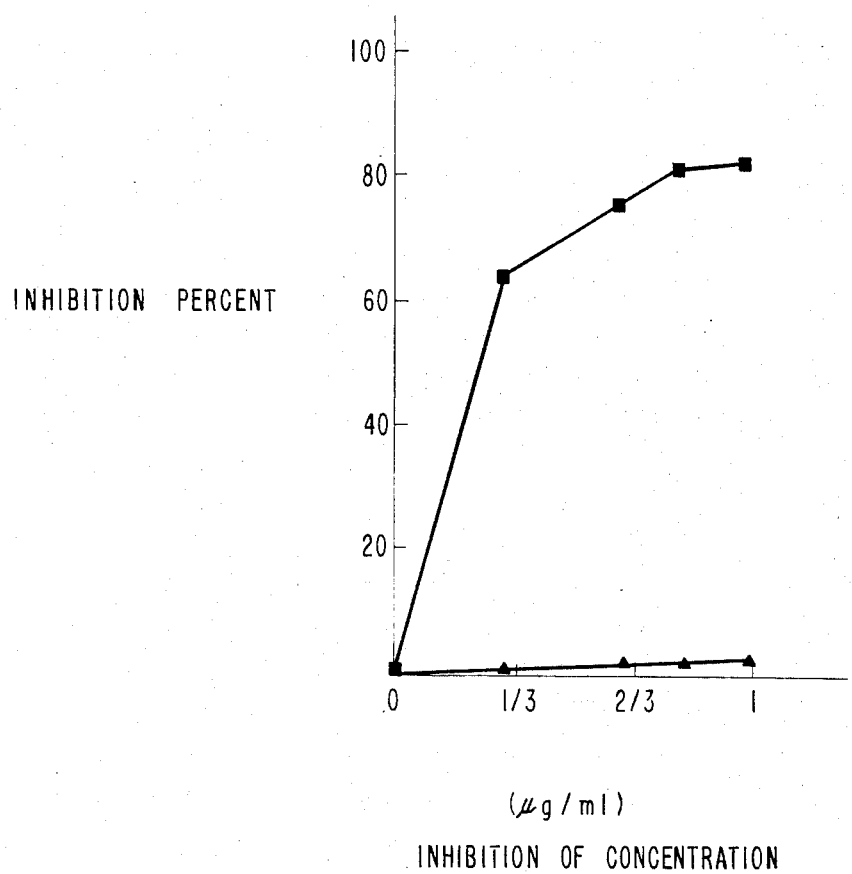
Figure 4:
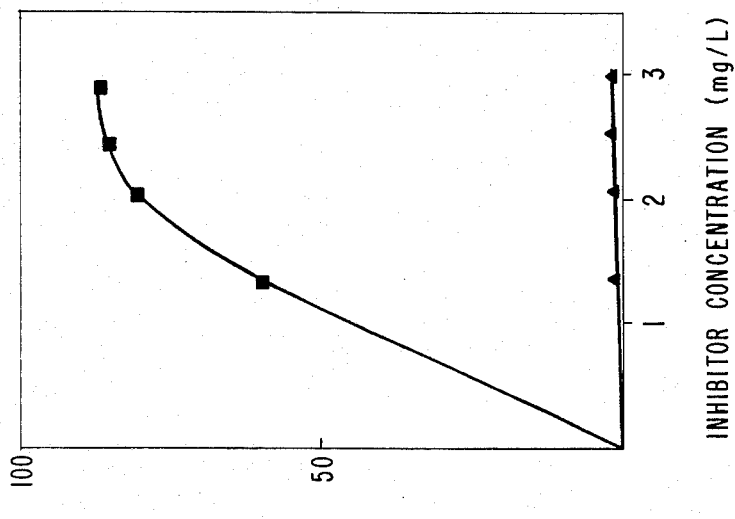
Figure 5:
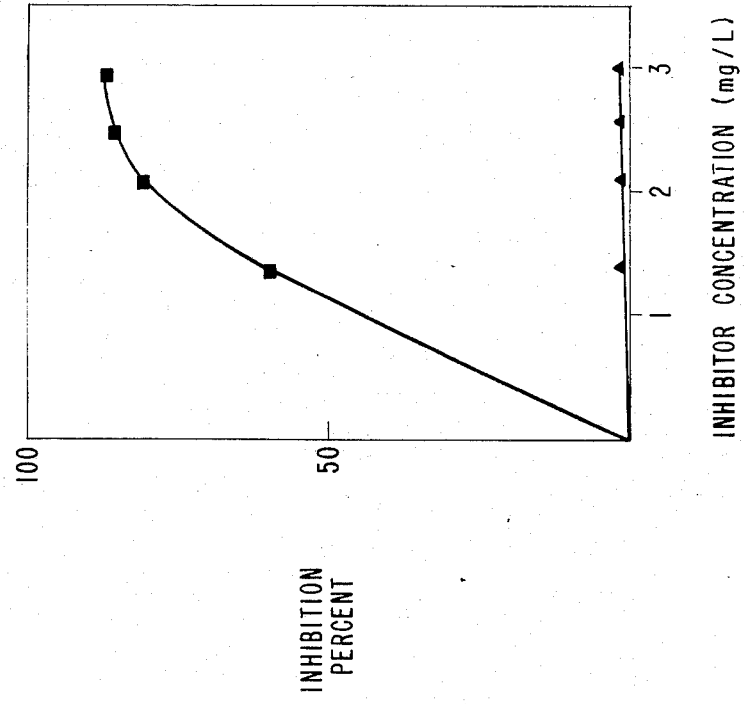
Figure 6:
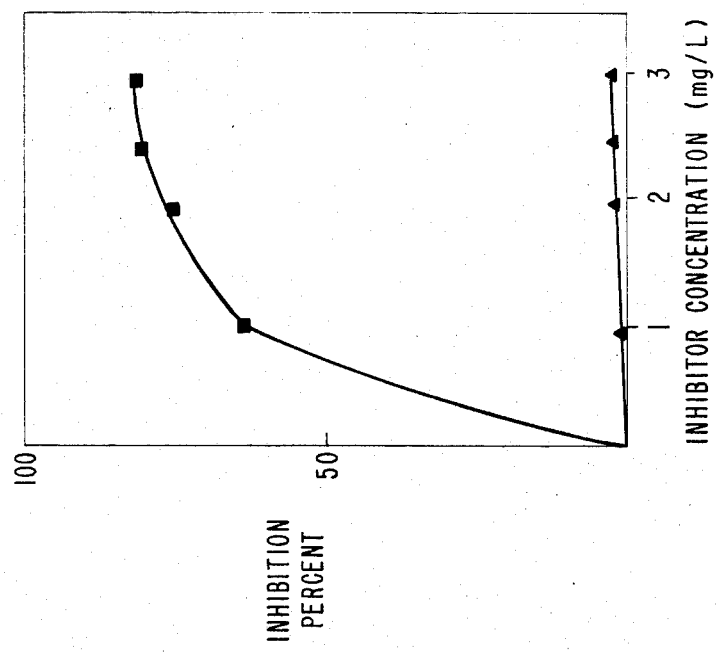

Using the amylase DS test (Beckman Instrument Co.), the effects of the amylase inhibitor on human salivary amylase (square) and human pancreatic amylase (triangle) were measured and are shown in FIG. 3. As to these amylases, the inhibition tests were also carried out using Blue starch (Pharmacia AB; FIG. 4), maltotetraose (FIG. 5) and p-nitrophenylmaltoheptaoside (FIG. 6) as substrate, and the results are shown in FIGS. 4 to 6.

As can be seen from the figures, the amylase inhibitor specifically inhibits the salivary amylase and does not inhibit the pancreatic amylase.

8. Inhibition type

Figure 7:
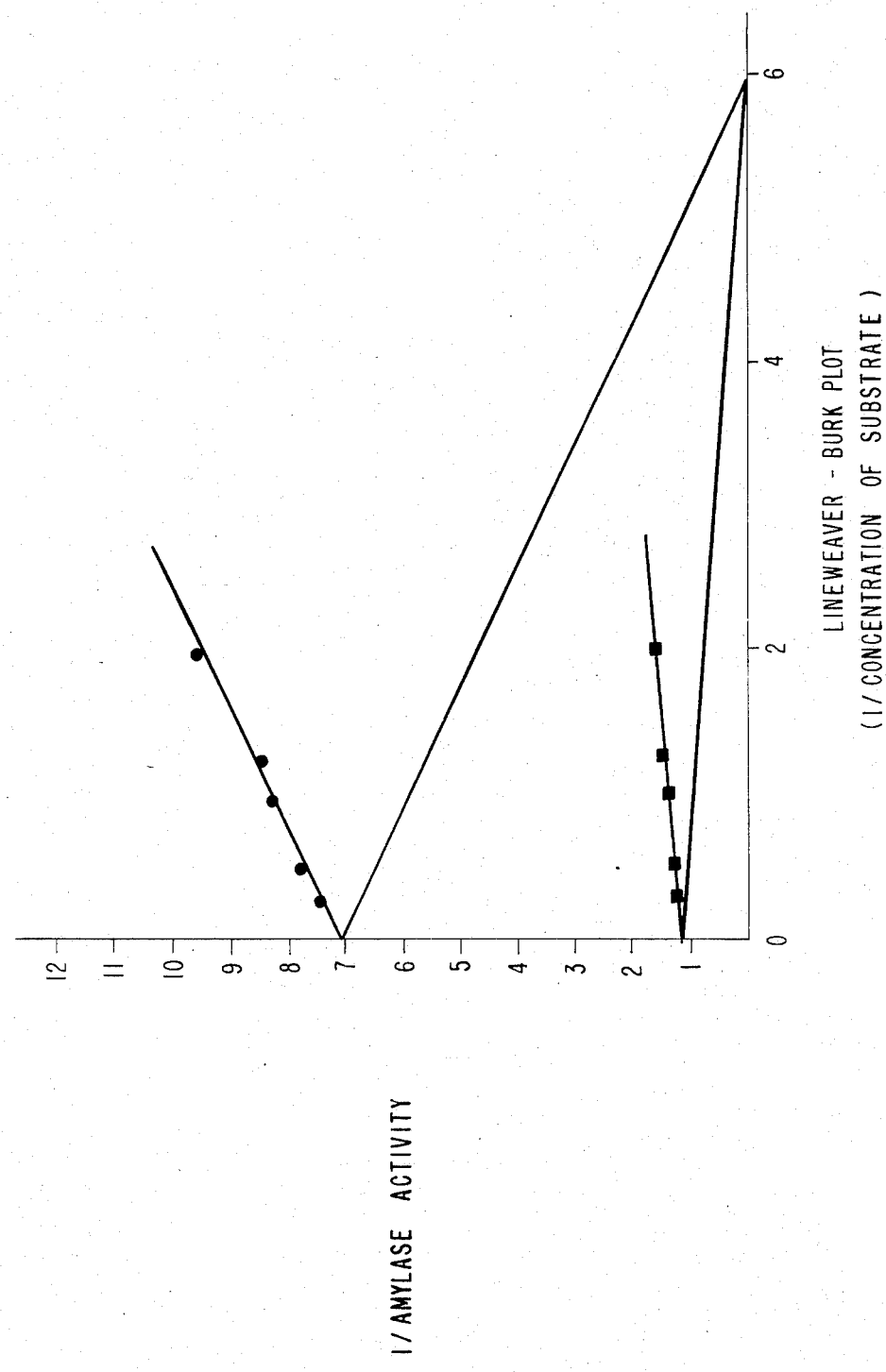

Using Blue starch (Pharmacia AB) as a substrate and human salivary amylase, the inhibition type of the amylase inhibitor was measured, and the results are shown in FIG. 7. In the figure, a circle indicates that the amylase inhibitor is present, and a square indicates that the amylase inhibitor is absent.

As can be seen from the figure, the amylase inhibitor of the present invention belongs to the non-competitive type. The inhibition constant ($K_i$) was $8.4 \times 10^{-9}$ M.

9. pH stability

Figure 8:
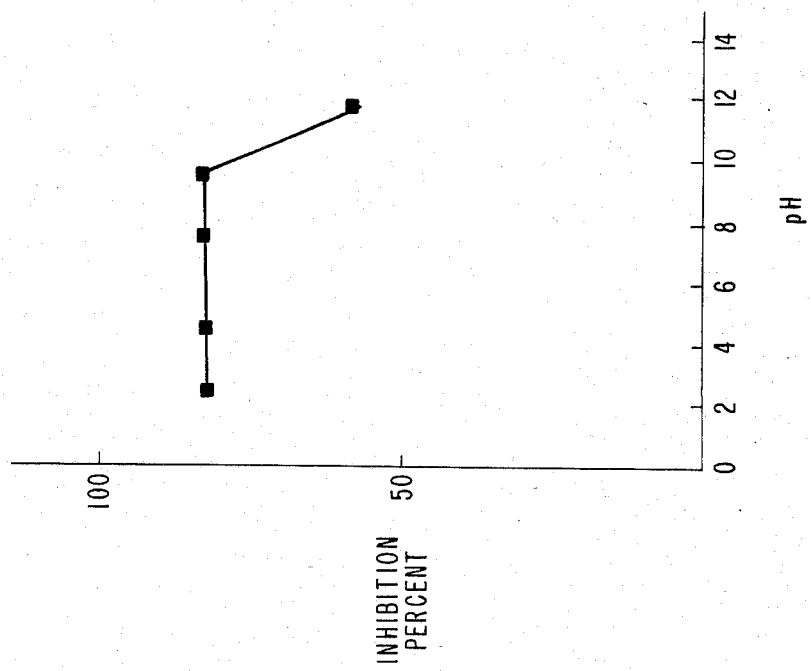

Aqueous solutions each containing 38 μg/ml of the amylase inhibitor which were previously adjusted to various pH values were heated at 37° C. for 30 minutes, and thereafter the inhibitory activities of the solutions on human salivary amylase were measured. The results are shown in FIG. 8.

10. Thermal stability

Figure 9:
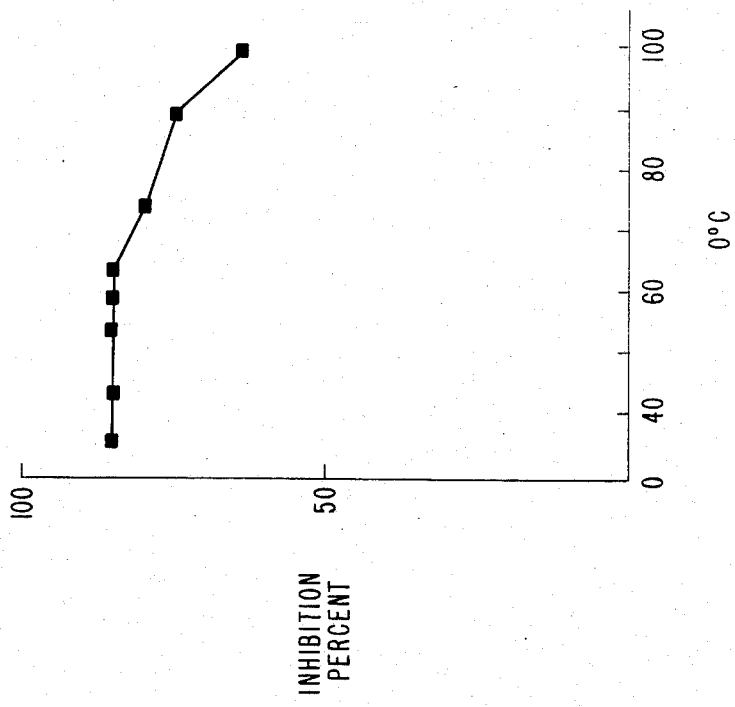

Aqueous solutions containing 38 μg/ml of the amylase inhibitor at a pH of 7.0 were heated at various temperatures for 30 minutes, and the remaining inhibitory activities of the solutions on human salivary amylase were measured. The results are shown in FIG. 9.

A comparison of the above-mentioned properties of the present amylase inhibitor with those of known amylase inhibitors shows that the present amylase inhibitor is fundamentally different from known amylase inhibitors. For example, every known amylase inhibitor obtained from wheat inhibits salivary amylase and pancreatic amylase. Furthermore, known amylase inhibitors obtained from wheat have molecular weights in the range of 13,000 to 20,000. In contradistinction, the present amylase inhibitor does not inhibit pancreatic amylase and has a molecular weight between about 23,000 and 24,000.

Figure 10:
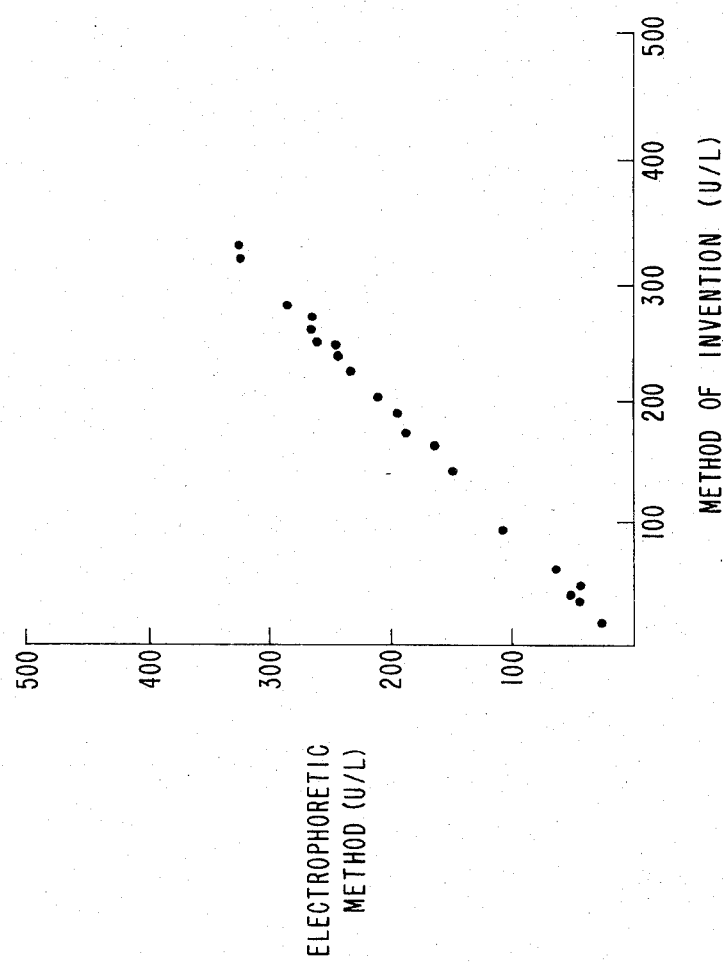

Samples of human urine containing various concentrations of amylase isoenzymes were measured by the method using the amylase inhibitor Sain obtained in Example 1 and by the conventional electrophoretic method and the results were compared as shown in FIG. 10. As can be seen from the figure, the data of the method using the amylase inhibitor Sain correlated with those of the conventional method.

Assay of amylase activity

One tablet of Blue starch (manufactured by Pharmacia AB) was added to 100 μl of an amylase solution, and incubated at 37° C. for 15 minutes. The absorbancy of the solution at 620 nm was measured, and the amylase activity is expressed in international units.

Assay of amylase inhibitory activity

Using human blood serum or urine as an amylase solution, 100 μl of the amylase solution was added to 100 μl of an amylase inhibitor solution, and the mixture was incubated at 37° C. for 5 minutes. One tablet of Blue starch (manufactured by Pharmacia AB) was added to the mixture, and the solution was incubated at 37° C. for 15 minutes. The absorbancy of the solution at 620 nm was measured, and one unit of amylase inhibitory activity is defined as the amount of inhibitory activity to inactivate 50% of the salivary amylase in the amylase solution.

Example of the production of the packing of the column for dye ligand affinity chromatography 100 ml of Sepharose 4B (manufactured by Pharmacia AB) was suspended in 200 ml of water. 4 g of sodium carbonate was added to the suspension, to make the suspension alkaline. One gram of reactive red (made by Sigma Chemicals Co.) was added to the alkaline suspension, and reacted at 40° C. for 40 hours. After the reaction, the suspension was filtered, and the residue was washed 10 times with 500 ml of water and then 2 times with 500 ml of acetone. The immobilized reactive red thus obtained was stored at 4° C., and it was found that the immobilized reactive red was stable for more than several months.

Example 1

1000 g of wheat flour produced from hard wheat (manufactured by Nisshin Flour Milling Co., Ltd.) was suspended in 8 volumes of water, and the suspension was stirred at room temperature for 1 hour. The wheat flour was filtered off, and washed with a small amount of water to obtain 6 l of a crude extract.

3 kg of ammonium sulfate was dissolved in the crude extract, and was allowed to stand for 1 hour at room temperature. The precipitates formed were collected by centrifuging, and dialyzed for one day against distilled water. The dialyzate was then lyophilized.

120 ml of the immobilized reactive red obtained in the above-mentioned Example was packed in a column. One gram of the lyophilized product was dissolved in 100 ml of 10 mM phosphate buffer solution having a pH of 6.0, and the solution was passed downwardly through the above column. The adsorbates on the immobilized reactive red were developed by means of gradient elution by first using 10 mM phosphate buffer solution having a pH of 6.0 then using acetone where the concentration of the acetone was continuously varied from 0 to 40 v/v%. The effluent of the column was fractionated into 9 ml portions by using a fraction collector. Inhibitory activity on salivary amylase and that on pancreatic amylase of each fraction were measured, and the fractions which specifically inhibited salivary amylase were collected.

The collected fractions were dialyzed for one day against water, and the residue was concentrated to one tenth of its original volume. The concentrate was diluted with tris-HCl buffer solution having a pH of 7.4, and the diluted concentrate was passed through the column where 20 ml of the ion-exchange resin DE-52 (made by Whatman Co.) was packed at the rate of 3 ml/hr. The effluent was fractionated into 2.1 ml portions by using a fraction collector. Ultraviolet absorption of each fraction at 280 nm was measured, and those fractions which indicated absorption, were also measured for amylase inhibitory activity.

The fractions having amylase inhibitory activity were collected, and dialyzed for one day against distilled water. The residue was lyophilized to obtain 0.1 g of the amylase inhibitor Sain in the form of white powder.

Example 2

1000 g of durum wheat flour was treated according to the same manner as employed in Example 1 except that ion-exchange chromatography was replaced by dye ligand affinity chromatography to obtain 0.11 g of a white powder. Amylase inhibitory activity, molecular weight, ultraviolet absorption and isoelectric point of this white powder were measured, and it was confirmed that the white powder was substantially identical with the white powder obtained in Example 1.

We claim:

1. An amylase inhibitor having inhibitory activity on human salivary amylase and which exhibits a ratio of the inhibition rate against pancreatic amylase to the inhibition rate against salivary amylase of less than 0.1, said inhibitor having the following characteristics:
   (a) a molecular weight of between about 23,000 and 24,000 as determined by gel filtration using Sephadex G-100;
   (b) an ultraviolet absorption spectrum of a 0.22 percent aqueous solution of said inhibitor substantially as shown in FIG. 1;
   (c) an infrared absorption spectrum of said inhibitor substantially as shown in FIG. 2;
   (d) an isoelectric point of said inhibitor of 5.0; and
   (e) an amino acid composition substantially as follows:

| Tyr | 17 | Ser | 12 |
|-----|----|----|----|
| Leu | 6 | Thr | 6 |
| Ile | 4 | Asp | 17 |
| Met | 10 | Arg | 9 |
| Val | 24 | His | 2 |
| Ala | 24 | Lys | 9 |
| Gly | 22 | Phe | 5 |
| Pro | 11 | ½ Cys | 14 |
| Glu | 22. | | |

2. A process for producing the amylase inhibitor of claim 1 comprising treating hard wheat or durum wheat with water or an aqueous solvent, and recovering the amylase inhibitor by dye ligand affinity chromatography.